United States Patent
Sakaki et al.

(10) Patent No.: US 8,519,184 B2
(45) Date of Patent: Aug. 27, 2013

(54) SYNTHESIS OF RARE EARTH METAL EXTRACTANT

(75) Inventors: Kazuaki Sakaki, Echizen (JP); Hiroto Sugahara, Echizen (JP); Tetsuya Ohashi, Echizen (JP); Tetsuya Kume, Echizen (JP); Masahiko Ikka, Echizen (JP); Hirochika Naganawa, Ibaraki (JP); Kojiro Shimojo, Ibaraki (JP)

(73) Assignees: Shin-Etsu Chemical Co., Ltd., Tokyo (JP); Nissin Chemical Industry Co., Ltd., Echizen-shi (JP)

( * ) Notice: Subject to any disclaimer, the term of this patent is extended or adjusted under 35 U.S.C. 154(b) by 0 days.

(21) Appl. No.: 13/176,214

(22) Filed: Jul. 5, 2011

(65) Prior Publication Data
US 2012/0004458 A1 Jan. 5, 2012

(30) Foreign Application Priority Data
Jul. 5, 2010 (JP) ................................. 2010-153161

(51) Int. Cl.
*C07C 229/22* (2006.01)
(52) U.S. Cl.
USPC .......................................................... 562/567
(58) Field of Classification Search
CPC .................................................... C07C 235/06
See application file for complete search history.

(56) References Cited

U.S. PATENT DOCUMENTS
2003/0176641 A1* 9/2003 Gokel et al. .................. 530/329

FOREIGN PATENT DOCUMENTS
JP 2007-327085 A 12/2007
WO 03/059937 A2 7/2003

OTHER PUBLICATIONS

European Search Report dated Oct. 25, 2011, issued in corresponding European Patent Application No. 11172262.5.
Schlesinger et al.; "Replacing proline at the apex of heptapeptide-based chloride ion transporters alters their properties and their ionophoretic efficacy"; New Journal of Chemistry, vol. 27, 2003, pp. 60-67, XP002660654.(cited in European Search Report dated Oct. 25, 2011).

* cited by examiner

*Primary Examiner* — Paul A Zucker
(74) *Attorney, Agent, or Firm* — Westerman, Hattori, Daniels & Adrian, LLP

(57) ABSTRACT

A rare earth metal extractant in the form of a dialkyl diglycol amic acid is synthesized by reacting diglycolic anhydride with a dialkylamine in a synthesis medium. A molar ratio (B/A) of dialkylamine (B) to diglycolic anhydride (A) is at least 1.0. A non-polar or low-polar solvent in which the dialkyl diglycol amic acid is dissolvable is used as the synthesis medium.

15 Claims, 1 Drawing Sheet

SYNTHESIS OF RARE EARTH METAL EXTRACTANT

CROSS-REFERENCE TO RELATED APPLICATION

This non-provisional application claims priority under 35 U.S.C. §119(a) on patent application Ser. No. 2010-153161 filed in Japan on Jul. 5, 2010, the entire contents of which are hereby incorporated by reference.

TECHNICAL FIELD

This invention relates to a method for synthesizing an extractant for extracting and separating a selected rare earth element from a mixture of rare earth elements, specifically from a mixture of at least two light rare earth elements (La, Ce, Pr, Nd, Sm, and Eu) or from a mixture of at least one light rare earth element and at least one other rare earth element inclusive of yttrium.

BACKGROUND ART

In the modern society, rare earth elements are used in a wide variety of applications, for example, as rare earth magnets, phosphors, and electronic and electric materials in nickel hydrogen batteries. With respect to the supply of rare earth elements, a crisis of the rare earth resource is highlighted because the producers are limited, the price lacks stability, and the demand is expected to surpass the supply in the near future. For these reasons, many attempts are made to reduce the amount of rare earth element used and to develop a replacement. At the same time, it is desired to establish a recycle system for recovering rare earth elements as one valuable from in-process scraps produced during manufacture of products and municipal wastes like electric and electronic appliances collected from cities. Also there is an urgent need for the research and development of new rare earth mines.

Known methods for separating rare earth elements include column extraction (or solid to liquid extraction) using ion exchange resins, and solvent extraction (or liquid to liquid extraction). Although the column extraction (or solid to liquid extraction) method is simple in apparatus and easy in operation as compared with the solvent extraction, it is small in extraction capacity and discourages rapid treatment. The column extraction method is thus used in the removal of a metal when the concentration of a metal to be extracted in a solution is low, that is, when the metal to be extracted is present as an impurity, as well as in the waste water treatment. On the other hand, the solvent extraction (or liquid to liquid extraction) method needs a complex apparatus and cumbersome operation as compared with the column extraction, but provides for a large extraction capacity and rapid treatment. The solvent extraction method is thus used in industrial separation and purification of metal elements. For the separation and purification of rare earth elements that requires efficient treatment of a large volume through continuous steps, the solvent extraction method capable of such efficient treatment is often used.

In the solvent extraction method, an aqueous phase consisting of an aqueous solution containing metal elements to be separated is contacted with an organic phase consisting of an extractant for extracting a selected metal element and an organic solvent for diluting the extractant. Then the metal element is extracted with the extractant for separation.

Known extractants used in the art include tributyl phosphate (TBP), carboxylic acids (e.g., Versatic Acid 10), phosphoric acid esters, phosphonic acid compounds, and phosphinic acid compounds. These extractants are commercially available. A typical phosphoric acid ester is di-2-ethylhexylphosphoric acid (D2EHPA), a typical phosphonic acid compound is 2-ethylhexylphosphonic acid-mono-2-ethylhexyl ester (PC-88A by Daihachi Chemical Industry Co., Ltd.), and a typical phosphinic acid compound is bis(2,4,4 trimethylpentyl)phosphinic acid (Cyanex 272 by Cytec Industries).

The separation efficiency of the solvent extraction method depends on a separation ability of the metal extractant, specifically a separation factor. As the separation factor is higher, the separation efficiency of the solvent extraction method is higher, which enables simplification of separating steps and scale-down of the separation apparatus, making the process efficient and eventually leading to a cost reduction. A low separation factor, on the other hand, makes the separation process complex and poses a need for a large-scale separation apparatus.

Even PC-88A which is known to have a high separation factor for rare earth elements among the currently commercially available extractants has a low separation factor between elements of close atomic numbers, for example, a separation factor of less than 2, specifically about 1.4 between neodymium and praseodymium which are allegedly most difficult to separate among rare earth elements. The separation factor of this value is not sufficient for separation between neodymium and praseodymium. To separate them at an acceptable purity, a large-scale apparatus must be installed at the expense of cost. For more efficient separation of these elements, there is a desire for the development of an extractant having a higher separation factor than in the prior art and an extracting/separating method using the same.

Dialkyl diglycol amic acids are known from JP-A 2007-327085 as the metal extractant having a high separation factor with respect to rare earth elements, specifically light rare earth elements such as lanthanum (La), cerium (Ce), praseodymium (Pr), neodymium (Nd), and samarium (Sm). Using this extractant in solvent extraction, the extraction/separation step of rare earth elements, specifically light rare earth elements can be made more efficient. In fact, better results are obtained from the extraction/separation step of light rare earth elements using dialkyl diglycol amic acid on a laboratory scale.

When dialkyl diglycol amic acid was used as the metal extractant, satisfactory results were confirmed in a light rare earth element extraction/separation experiment which was conducted at a rare earth element concentration ($C_A$: 0.01 mol/L$\leq C_A \leq$0.7 mol/L) and a corresponding metal extractant concentration ($C_0$: 0.1 mol/L$\leq C_0 \leq$1.5 mol/L) which were practical operating conditions of the rare earth element separating process and in a light rare earth element extraction/separation experiment using a countercurrent flow multistage mixer/settler of a practically operating apparatus.

The dialkyl diglycol amic acid exhibits a satisfactory separation factor in its performance as the metal extractant for separating light rare earth elements, as mentioned above, and its operating conditions have been surveyed. However, its synthesis has not been fully established.

The known method for synthesizing the dialkyl diglycol amic acid is in accord with the following reaction scheme.

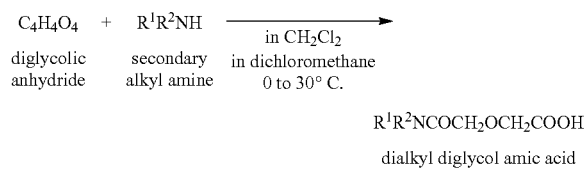

R¹R²NCOCH₂OCH₂COOH
dialkyl diglycol amic acid

Herein $R^1$ and $R^2$ are each independently alkyl, and at least one is a straight or branched alkyl group of at least 6 carbon atoms.

First, diglycolic anhydride is suspended in dichloromethane. A secondary alkylamine in an amount slightly less than an equimolar amount to the diglycolic anhydride is dissolved in dichloromethane and the resulting solution is mixed with the suspension at 0 to 30° C. As diglycolic anhydride reacts, the mixed solution becomes clear. The reaction is completed when the solution becomes clear. This is followed by removal of water-soluble impurities by washing with deionized water, removal of water with a dehydrating agent (e.g., sodium sulfate), filtration, and solvent removal. Recrystallization from hexane is repeated plural times for purification, yielding the desired product (see JP-A 2007-327085).

This synthesis method uses as the synthesis medium dichloromethane which is one of the harmful substances listed in several environmental pollution control laws, regulations and Pollutant Release and Transfer Register (PRTR) in Japan and the corresponding regulations in many countries. It is recommended to avoid the substance.

The above synthesis method allegedly gives a yield of more than 90% because it is conducted only on a laboratory scale where the amount of synthesis is several grams.

However, a prominent drop of yield occurs when the synthesis is enlarged to a scale of several kilograms or more. In fact, in a synthesis experiment conducted on a scale of several hundreds of grams, the yield decreases below 80%. Such a yield drop is unwanted.

Citation List

Patent Document 1: JP-A 2007-327085

SUMMARY OF INVENTION

An object of the invention is to provide a method for synthesizing a rare earth metal extractant without a need for dichloromethane which is used as reaction medium in the prior art synthesis, the method being capable of improving the yield of the reaction product and the efficiency of synthesis.

The inventors have found that in the synthesis of a dialkyl diglycol amic acid serving as a rare earth metal extractant, better results are obtained by reacting reactants, diglycolic anhydride and a dialkylamine in a specific synthesis medium. Used as the synthesis medium is a non-polar or low-polar solvent in which the dialkyl diglycol amic acid is dissolvable and which will serve as an organic solvent to form an organic phase in subsequent solvent extraction. This method permits the dialkyl diglycol amic acid to be effectively synthesized in high yields.

The invention provides a method for synthesizing a rare earth metal extractant in the form of a dialkyl diglycol amic acid having the general formula (1):

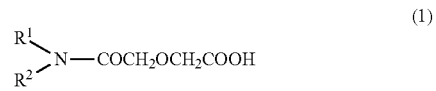

wherein $R^1$ and $R^2$ are each independently alkyl, at least one being a straight or branched alkyl group of at least 6 carbon atoms, including the step of reacting diglycolic anhydride with a dialkylamine in a synthesis medium. The dialkylamine (B) and diglycolic anhydride (A) are present in a molar ratio (B/A) of at least 1.0. Preferably the molar ratio (B/A) of dialkylamine (B) to diglycolic anhydride (A) is in a range of 1.0 to 1.2. The synthesis medium used herein is a non-polar or low-polar solvent in which the dialkyl diglycol amic acid is dissolvable and which will serve as an organic solvent to form an organic phase in subsequent solvent extraction. The non-polar or low-polar solvent is typically selected from among toluene, xylene, hexane, isododecane, kerosine, and higher alcohols.

Also preferably the synthesis medium is used in such an amount that the reaction solution at the end of reaction may contain the dialkyl diglycol amic acid in a concentration $C_0$ of 0.1 mol/L to 1.5 mol/L.

ADVANTAGEOUS EFFECTS OF INVENTION

According to the method of the invention, a dialkyl diglycol amic acid which is an extractant having an improved separation factor for light rare earth elements can be effectively synthesized in high yields without a need for a harmful solvent, dichloromethane. The method is of great worth in the industry.

DESCRIPTION OF EMBODIMENTS

Figure 1:
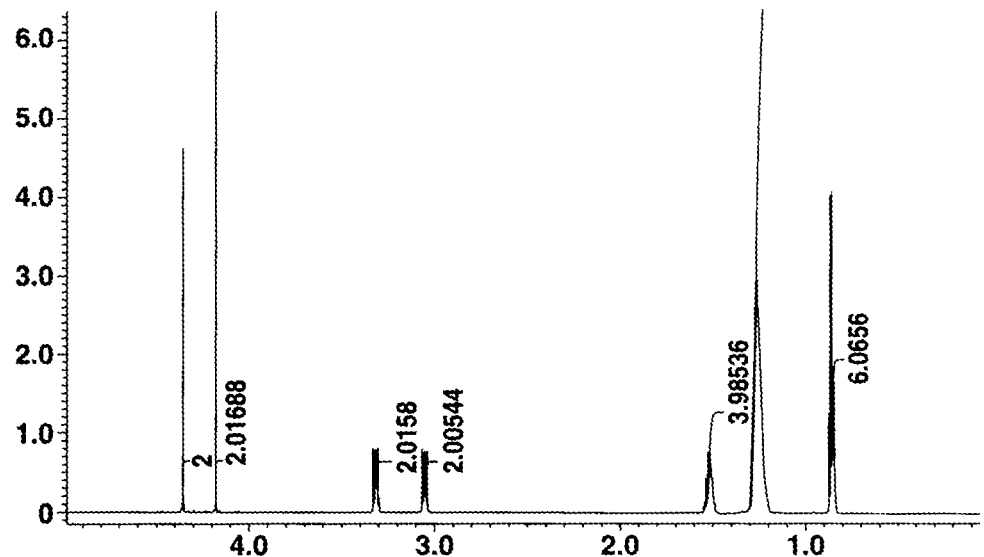
FIG. 1 is a ¹H-NMR chart of the reaction product of Example 1.

The invention pertains to a rare earth metal extractant which is a dialkyl diglycol amic acid having the general formula (1).

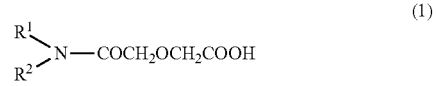

Herein $R^1$ and $R^2$ are each independently alkyl, at least one of $R^1$ and $R^2$ being a straight or branched alkyl group of at least 6 carbon atoms, preferably 6 to 18 carbon atoms, and more preferably 7 to 12 carbon atoms. If the carbon count is less than 6, the compound failing to play the role of extractant because it is less lipophilic so that the organic phase lacks stability and exhibits poor separation from the aqueous phase, and because the dissolution of the extractant itself in aqueous phase becomes noticeable. An excessive carbon count contributes to no improvements in basic abilities like extraction and separation abilities despite the increased cost of extractant manufacture. As long as lipophilic nature is ensured, if one of $R^1$ and $R^2$ has a carbon count of at least 6, then the other may be of less than 6 carbon atoms. For example, a compound of formula (1) wherein two octyl (—$C_8H_{17}$) groups are introduced is most preferred, which is named N,N-dioctyl-3-oxapentane-1,5-amic acid or dioctyl diglycol amic acid (abbreviated as DODGAA, hereinafter).

According to the invention, the dialkyl diglycol amic acid is synthesized by reacting diglycolic anhydride with a dialkylamine in a synthesis medium. The synthesis medium used herein is a non-polar or low-polar solvent in which the dialkyl diglycol amic acid is dissolvable and which will serve as an organic solvent to form an organic phase in subsequent solvent extraction. For example, diglycolic anhydride is suspended in an organic solvent (which will form an organic phase in subsequent solvent extraction), and the dialkylamine is dissolved in an organic solvent (which will form an organic phase in subsequent solvent extraction). The suspension and the solution are mixed together for reaction to take place. The dialkylamine used herein is a secondary alkylamine having alkyl groups corresponding to $R^1$ and $R^2$ in the dialkyl diglycol amic acid of formula (1).

The organic solvent which is used herein as the synthesis medium and which will form an organic phase in subsequent solvent extraction is a non-polar or low-polar solvent in which the dialkyl diglycol amic acid is dissolvable. The non-polar or low-polar solvent is a solvent having a dielectric constant of up to 15, for example, having a low solubility in water, providing an appropriate solubility for the extractant, having a low specific gravity, and facilitating an extraction ability. Preferably the non-polar or low-polar solvent is selected from among toluene, xylene, hexane, isododecane, kerosine, and higher alcohols such as straight chain alcohols of 5 to 8 carbon atoms. Use of such an organic solvent as the synthesis medium eliminates a need for removal of the synthesis medium and ensures that the organic solvent present in the reaction solution may be used as the organic phase for solvent extraction directly or, if necessary, after an additional amount of the organic solvent is added so as to provide the organic phase with a desired metal extractant concentration for solvent extraction.

If the synthesis medium is a solvent other than the non-polar or low-polar solvent in which the dialkyl diglycol amic acid is dissolvable and which will serve as an organic solvent to form an organic phase in subsequent solvent extraction, then the synthesis medium must be removed after the reactants are mixed and reacted therein.

In the reaction step, an amount (B mol) of dialkylamine and an amount (A mol) of diglycolic anhydride are used in a molar ratio (B/A) of at least 1.0, preferably $1.0 \leq B/A \leq 1.2$, and more preferably $1.0 \leq B/A \leq 1.1$. The resulting reaction product contains unreacted dialkylamine as well as the desired dialkyl diglycol amic acid. In the prior art method, plural times of recrystallization are necessary to remove the unreacted dialkylamine. It has been found that when solvent extraction is carried out using dialkyl diglycol amic acid having dialkylamine left therein, no problems arise with respect to separation efficiency and phase separation, ensuring effective extraction and separation. Specifically, even if the dialkylamine is left in the metal extractant and the organic phase during solvent extraction, it does not become an inhibitory factor to extraction and separation and there is no need to remove it as an impurity. As a result, the synthesis process can be simplified. A loss of the reaction product by recrystallization is minimized. These contribute to improved yields.

If B/A>1.2, the resulting reaction product may contain an excess of unreacted dialkylamine as well as the desired dialkyl diglycol amic acid. This reaction product may be used as the extractant because no problems arise with respect to separation efficiency and phase separation during solvent extraction. However, use of excess dialkylamine is meaningless. Also the cost of reactants for synthesis increases, rendering the method less cost effective.

If B/A<1.0, which means an excess of diglycolic anhydride for reaction, the desired dialkyl diglycol amic acid is obtained as the reaction product, in which unreacted diglycolic acid may remain. When solvent extraction is carried out using dialkyl diglycol amic acid having diglycolic acid left therein, no satisfactory separation ability is available and the solution becomes white turbid because clad is formed between organic phase and aqueous phase. This results in poor phase separation, failing in normal extraction and separation. This is because the diglycolic acid remaining along with the metal extractant, dialkyl diglycol amic acid forms a complex with a rare earth metal ion, inhibiting satisfactory extraction and separation. That is, diglycolic acid becomes an inhibitory factor to extraction. To obtain diglycolic acid-free dialkyl diglycol amic acid as the rare earth metal extractant capable of normal extraction and separation, the step of removing unreacted diglycolic acid is necessary as in the prior art method. Specifically, the water-soluble diglycolic acid must be removed by removing the synthesis solvent and washing the reaction product with water. Upon water washing, however, the dialkyl diglycol amic acid having a very low solubility in water crystallizes and precipitates in the solvent (for example, a solubility of DODGAA in water is $6.2 \times 10^{-6}$ mol/L). In order to use the dialkyl diglycol amic acid in crystallized form as the rare earth metal extractant, filtration and drying steps are needed. The process becomes less efficient because extra steps are necessary as compared with the range of $1.0 \leq B/A \leq 1.2$.

In a preferred embodiment of the method, the synthesis medium is used in such an amount that the reaction solution at the end of reaction may contain the dialkyl diglycol amic acid in a concentration of 0.1 mol/L to 1.5 mol/L. Specifically, the amount of dialkyl diglycol amic acid produced by the synthesis reaction is previously computed from the amounts of reactants by the stoichiometry in accord with the reaction scheme, and the amount of the synthesis medium is adjusted such that the concentration $C_0$ of metal extractant or dialkyl diglycol amic acid in the reaction solution may fall in a range: $0.1 \text{ mol/L} \leq C_0 \leq 1.5$ mol/L, and more preferably 0.2 mol/L $\leq C_0 \leq 1.0$ mol/L. The reaction solution obtained in this preferred embodiment may be used as the organic phase in subsequent solvent extraction directly, i.e., without a need for concentration adjustment during subsequent solvent extraction, for example, by adding a solvent such that the metal extractant in the organic phase may be present in a predetermined concentration applicable in the practical extraction step.

In case the extractant concentration $C_0$<0.1 mol/L, the dialkyl diglycol amic acid is produced by synthesis. However, when this reaction product is used in solvent extraction on an actual operation scale, the metal extractant concentration in the organic phase is so low that only an aqueous solution having a concentration of up to 0.03 mol/L of rare earth elements may be treated. This entails a larger scale of separation apparatus and a cost increase. It is very difficult, inefficient and impractical to increase the extractant concentration from such a low level to a high level for actual operation.

On the other hand, it is often difficult to set an extractant concentration $C_0$>1.5 mol/L, from considerations of the solubility of the dialkyl diglycol amic acid in organic solvents used in general solvent extraction methods. After the synthesis reaction, a portion of the dialkyl diglycol amic acid which is not dissolved in the solvent may crystallize and precipitate out. Although the extra portion may be dissolved by adding a solvent, surfactant or entrainer, the reaction product solution is not efficient as the organic phase for solvent extraction because the control of conditions for stable operation becomes more complex.

EXAMPLE

Examples are given below by way of illustration and not by way of limitation.

Example 1 and Comparative Example 1

Synthesis of Rare Earth Metal Extractant and Extraction/separation Test

DODGAA was synthesized by the method of the invention. The DODGAA thus synthesized was examined for an ability to separate rare earth metals from a mixture thereof by the solvent extraction method.

First, 34.8 g (0.3 mol) of diglycolic anhydride was suspended in 400 mL of hexane as synthesis medium. Separately, 72.4 g (0.3 mol) of dioctylamine was dissolved in 100 mL of hexane. With stirring, the dioctylamine solution was added dropwise to the diglycolic anhydride suspension.

Stirring was continued at room temperature until it was confirmed that the solution became clear as a result of reaction of diglycolic anhydride. The reaction product was obtained in hexane solution (Example 1).

In Comparative Example 1, the same procedure as above was repeated aside from using acetone as the reaction medium. The reaction product was obtained in acetone solution.

Figure 2:
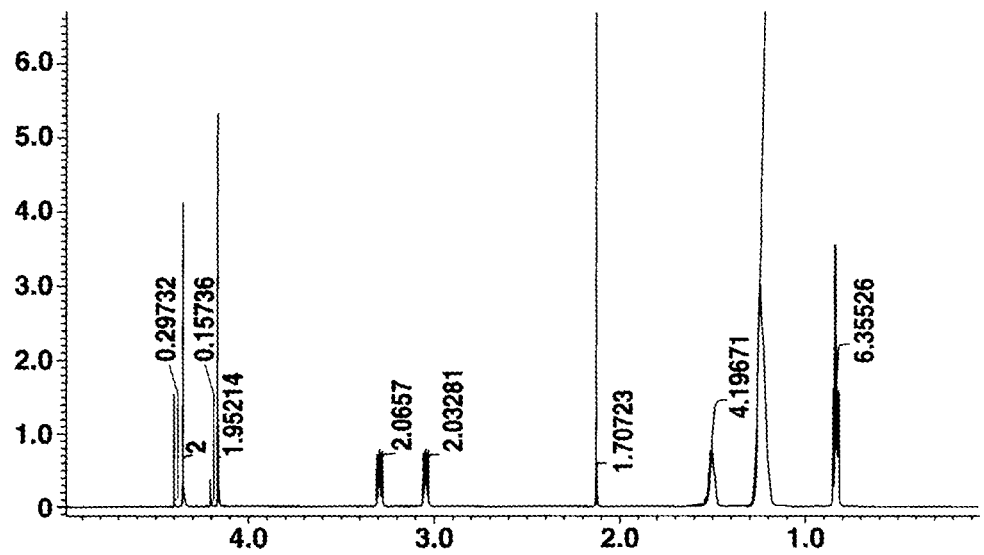
FIG. 2 is a ¹H-NMR chart of the reaction product of Comparative Example 1.

Samples of the reaction products in Example 1 and Comparative Example 1 were taken out and vacuum dried for solvent removal, before they were analyzed by $^1$H-NMR spectroscopy as shown in FIGS. 1 and 2, respectively. The reaction products in Example 1 and Comparative Example 1 were identified to be DODGAA.

An extraction/separation test was performed. The concentration of DODGAA in the reaction product solution of Example 1 or Comparative Example 1 was computed from the amounts of reactants and synthesis medium. The reaction product solution was diluted with hexane to form an organic solution having a DODGAA concentration of 0.3 mol/L, which might become an organic phase.

An aqueous solution containing mixed rare earth metals was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted into the organic phase was back-extracted into the aqueous hydrochloric acid solution. The concentrations of praseodymium and neodymium in the aqueous phase and the back-extracted aqueous hydrochloric acid solution were measured by an ICP atomic emission spectrometer ICP-7500 (Shimadzu Corp.). The Nd/Pr separation factor and phase separation are reported in Table 1.

TABLE 1

| | Synthesis medium | Nd/Pr separation factor | Phase separation |
|---|---|---|---|
| Example 1 | hexane | 2.5 | definite |
| Comparative Example 1 | acetone | 2.5 | indefinite |

For the reaction product obtained in Example 1, its Nd/Pr separation factor indicative of the separation ability as a metal extractant was satisfactory, and the phase separation state was definite. For the reaction product obtained in Comparative Example 1, its Nd/Pr separation factor was satisfactory, but it was inadequate for solvent extraction as demonstrated by an indefinite phase separation state. It is evident that when a dialkyl diglycol amic acid is synthesized using as the synthesis medium a non-polar or low-polar solvent in which the dialkyl diglycol amic acid is dissolvable and which will serve as an organic solvent to form an organic phase in subsequent solvent extraction, the process becomes very efficient due to an eliminated need for solvent removal.

Examples 2 to 5 and Comparative Example 2

An amount (designated A in Table 2) of diglycolic anhydride was suspended in 40 mL of hexane. Separately, an amount (designated B in Table 2) of dioctylamine was dissolved in 10 mL of hexane. With stirring, the dioctylamine solution was added dropwise to the diglycolic anhydride suspension. Stirring was continued at room temperature until it was confirmed that the solution became clear as a result of reaction of diglycolic anhydride. The reaction product was obtained in hexane solution. Table 2 also reports a ratio B/A that is a ratio of the amount (B mmol) of dioctylamine to the amount (A mmol) of diglycolic anhydride.

Samples of the reaction products were taken out and vacuum dried for hexane removal, before they were analyzed by $^1$H-NMR spectroscopy, with DODGAA detected in all the products. A minor amount of dioctylamine was detected in Examples 2, 3 and 5 while a minor amount of diglycolic acid detected in Comparative Example 2.

An extraction/separation test was performed. The concentration of DODGAA in the reaction product solution was computed from the amounts of reactants and synthesis medium. The reaction product solution was diluted with hexane to form an organic solution having a DODGAA concentration of 0.3 mol/L, which might become an organic phase.

An aqueous solution containing mixed rare earth metals was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted into the organic phase was back-extracted into the aqueous hydrochloric acid solution. The concentrations of praseodymium and neodymium in the aqueous phase and the back-extracted aqueous hydrochloric acid solution were measured by an ICP atomic emission spectrometer ICP-7500 (Shimadzu Corp.). The extractant state, Nd/Pr separation factor, and phase separation are reported in Table 2.

TABLE 2

| | A<br>diglycolic<br>anhydride | | B<br>dioctylamine | | | Extractant state | Nd/Pr separation factor | Phase separation |
|---|---|---|---|---|---|---|---|---|
| | (g) | (mmol) | (g) | (mmol) | B/A | | | |
| Example 2 | 3.5 | 30.2 | 8.4 | 34.8 | 1.15 | liquid | 2.5 | definite |
| Example 3 | 3.5 | 30.2 | 8.0 | 33.1 | 1.10 | liquid | 2.5 | definite |
| Example 4 | 3.5 | 30.2 | 7.3 | 30.2 | 1.00 | liquid | 2.5 | definite |
| Example 5 | 3.5 | 30.2 | 9.0 | 37.3 | 1.24 | solid | 2.5 | definite |
| Comparative Example 2 | 3.9 | 33.6 | 7.3 | 30.2 | 0.90 | liquid | — | indefinite |

In Examples 2, 3 and 4 wherein a ratio of the amount (B mmol) of dioctylamine to the amount (A mmol) of diglycolic anhydride is $1.0 \leq B/A \leq 1.2$, the Nd/Pr separation factor indicative of the separation ability of a metal extractant and the phase separation were satisfactory.

In Example 5 wherein B/A>1.2, the Nd/Pr separation factor and the phase separation were satisfactory, but the reaction product was difficult to handle as compared with the other products because the excess dioctylamine in the reaction product solidified. In Comparative Example 2, the excess diglycolic anhydride became an inhibitory factor to extraction, causing indefinite phase separation, and the Nd/Pr separation factor could not be measured.

Examples 6 to 9

Diglycolic anhydride, 46.4 g (0.4 mol), was suspended in X mL of hexane. Separately, 96.6 g (0.4 mol) of dioctylamine was dissolved in Y mL of hexane. With stirring, the dioctylamine solution was added dropwise to the diglycolic anhydride suspension. Stirring was continued at room temperature until it was confirmed that the solution became clear as a result of reaction of diglycolic anhydride. The reaction product was obtained in hexane solution. The amounts X and Y of hexane as the reaction medium are shown in Table 3.

Samples of the reaction products were taken out and vacuum dried for hexane removal, before they were analyzed by $^1$H-NMR spectroscopy, with DODGAA detected in all the products. The concentration $C_0$ of the reaction product (DODGAA) in the hexane solution is shown in Table 3.

An extraction/separation test was performed using the hexane solution of the reaction product (DODGAA) directly as an organic solution which might become an organic phase.

An aqueous solution containing mixed rare earth metals was prepared by dissolving praseodymium chloride and neodymium chloride in water in a molar ratio Pr:Nd of 1:1 and a concentration (mol/L) of Pr+Nd as shown in Table 4 to form an aqueous solution which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted into the organic phase was back-extracted into the aqueous hydrochloric acid solution. The concentrations of praseodymium and neodymium in the aqueous phase and the back-extracted aqueous hydrochloric acid solution were measured by an ICP atomic emission spectrometer ICP-7500 (Shimadzu Corp.). The Nd/Pr separation factor and phase separation are reported in Table 4.

TABLE 3

| | Amount X (mL) of hexane | Amount Y (mL) of hexane | DODGAA Concentration $C_0$ (mol/L) |
|---|---|---|---|
| Example 6 | 3200 | 800 | 0.1 |
| Example 7 | 640 | 160 | 0.5 |
| Example 8 | 320 | 80 | 1.0 |
| Example 9 | 214 | 53 | 1.5 |

TABLE 4

| | Mixed rare earth metal concentration (mol/L) | Nd/Pr separation factor | Phase separation |
|---|---|---|---|
| Example 6 | 0.03 | 2.5 | definite |
| Example 7 | 0.10 | 2.5 | definite |
| Example 8 | 0.10 | 2.5 | definite |
| Example 9 | 0.50 | 2.5 | definite |

Examples 6 to 9 wherein the concentration $C_0$ (mol/L) of DODGAA was in the range: $0.1 \text{ mol/L} \leq C_0 \leq 1.5 \text{ mol/L}$ demonstrated a high separation factor and definite phase separation.

Japanese Patent Application No. 2010-153161 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for synthesizing a rare earth metal extractant in the form of a dialkyl diglycol amic acid having the general formula (1):

(1)

wherein $R^1$ and $R^2$ are each independently alkyl, at least one being a straight or branched alkyl group of 6 to 12 carbon atoms, comprising the step of reacting diglycolic anhydride with a dialkylamine in a synthesis medium, wherein dialkylamine (B) and diglycolic anhydride (A) are present in a molar ratio (B/A) in a range of 1.0 to 1.2, and the synthesis medium is a non-polar or low-polar solvent in which the dialkyl diglycol amic acid is dissolvable and which will serve as an organic solvent to form an organic phase in subsequent solvent extraction.

2. The method of claim 1 wherein the non-polar or low-polar solvent is selected from the group consisting of toluene, xylene, hexane, isododecane, kerosine, and straight chain alcohols of 5 to 8 carbon atoms.

3. The method of claim 1 wherein the synthesis medium is used in such an amount that the reaction solution at the end of reaction may contain the dialkyl diglycol amic acid in a concentration of 0.1 mol/L to 1.5 mol/L.

4. The method of claim 1 wherein the non-polar or low-polar solvent is a solvent having a dielectric constant of up to 15.

5. The method of claim 1 wherein the non-polar or low-polar solvent is selected from the group consisting of xylene, hexane, isododecane, kerosine, and straight chain alcohols of 5 to 8 carbon atoms.

6. The method of claim 1 wherein the non-polar or low-polar solvent comprises hexane.

7. The method of claim 1 wherein $R^1$ and $R^2$ are, respectively, a straight or branched alkyl group of 8 carbon atoms.

8. The method of claim 1 comprising the step of mixing the diglycolic anhydride suspended in the synthesis medium with the dialkylamine dissolved in the synthesis medium.

9. The method of claim 1 wherein the non-polar or low-polar solvent is selected from the group consisting of hexane, isododecane, kerosine, and straight chain alcohols of 5 to 8 carbon atoms.

10. A method for synthesizing a rare earth metal extractant in the form of a dialkyl diglycol amic acid having the general formula (1):

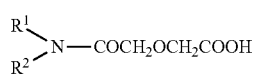

(1)

wherein $R^1$ and $R^2$ are each independently alkyl, at least one being a straight or branched alkyl group of 6 to 12 carbon atoms, comprising the step of reacting diglycolic anhydride with a dialkylamine in a synthesis medium, wherein dialkylamine (B) and diglycolic anhydride (A) are present in a molar ratio (B/A) of at least 1.0, and the synthesis medium is a non-polar or low-polar solvent in which the dialkyl diglycol amic acid is dissolvable and which will serve as an organic solvent to form an organic phase in subsequent solvent extraction, wherein the non-polar or low-polar solvent is selected from the group consisting of hexane, isododecane, kerosine, and straight chain alcohols of 5 to 8 carbon atoms.

11. The method of claim 10 wherein the molar ratio (B/A) of dialkylamine (B) to diglycolic anhydride (A) is in a range of 1.0 to 1.2.

12. The method of claim 10 wherein the synthesis medium is used in such an amount that the reaction solution at the end of reaction may contain the dialkyl diglycol amic acid in a concentration of 0.1 mol/L to 1.5 mol/L.

13. The method of claim 10 wherein the non-polar or low-polar solvent comprises hexane.

14. The method of claim 10 wherein $R^1$ and $R^2$ are, respectively, a straight or branched alkyl group of 8 carbon atoms.

15. The method of claim 10 comprising the step of mixing the diglycolic anhydride suspended in the synthesis medium with the dialkylamine dissolved in the synthesis medium.

* * * * *